US012765866B2

(12) United States Patent
Hiwale et al.

(10) Patent No.: US 12,765,866 B2
(45) Date of Patent: Oct. 20, 2026

(54) RELIABLIITY ASSESSMENT OF CARDIAC PARAMETER MEASUREMENTS

(71) Applicant: KONINKLIJKE PHILIPS N.V., Eindhoven (NL)

(72) Inventors: Sujitkmar Hiwale, Aurangabad (IN); Murtaza Bulut, Eindhoven (NL); Laurentia Johanna Huijbregts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/872,330

(22) PCT Filed: May 19, 2023

(86) PCT No.: PCT/EP2023/063528
§ 371 (c)(1),
(2) Date: Dec. 6, 2024

(87) PCT Pub. No.: WO2023/237315
PCT Pub. Date: Dec. 14, 2023

(65) Prior Publication Data
US 2025/0359853 A1 Nov. 27, 2025

(30) Foreign Application Priority Data
Jun. 7, 2022 (EP) .................................... 22177669

(51) Int. Cl.
*A61B 8/00* (2006.01)
*A61B 8/06* (2006.01)
*A61B 8/12* (2006.01)

(52) U.S. Cl.
CPC ............ *A61B 8/5276* (2013.01); *A61B 8/065* (2013.01); *A61B 8/12* (2013.01)

(58) Field of Classification Search
None
See application file for complete search history.

(56) References Cited

U.S. PATENT DOCUMENTS 8,965,490 B2 2/2015 Lee
10,716,537 B2 7/2020 Gregg
(Continued)

FOREIGN PATENT DOCUMENTS

KR 20190068368 A 6/2019

OTHER PUBLICATIONS

Dark et al., "The validity of trans-esophageal Doppler ultrasonography as a measure of cardiac output in critically ill adults", Intensive Care Med, vol. 30, pp. 2060-2066, Sep. 2004. (Year: 2004).*
(Continued)

*Primary Examiner* — Katherine L Fernandez

(57) ABSTRACT

A method (200) for assessing reliability of a cardiac parameter of a subject is disclosed. The method comprises receiving data (201) from a transesophageal echocardiography probe, a heart activity sensor, and a motion sensor, determining (202) a TEE cardiac parameter relating to the cardiac parameter estimated using data from the transesophageal echocardiography probe, determining a heart activity cardiac parameter relating to the cardiac parameter estimated using data from the heart activity sensor, determining (203) the cardiac parameter based on at least one of the TEE and heart activity parameters, assessing the reliability of the cardiac parameter based on the TEE and heart activity parameters and the data from the motion sensor, and transmitting to an output device, a feedback signal based on the reliability of the cardiac parameter. In accordance with the invention, the method further comprises determining (206) a cardiac parameter trend and whether the cardiac parameter trend exceeds a trend threshold, detecting motion of the
(Continued)

subject (220) during a first time period, based on the data of the motion sensor, and assessing the reliability of the cardiac parameter based on whether the cardiac parameter trend exceeds the trend threshold and on whether motion of the subject has been detected. Also disclosed are a computer program and a system (3) for implementing such a method.

20 Claims, 3 Drawing Sheets

(56) References Cited

U.S. PATENT DOCUMENTS

| | | | | |
|---|---|---|---|---|
| 2010/0056918 | A1 | 3/2010 | Sato | |
| 2012/0226126 | A1 | 9/2012 | Busse | |
| 2014/0005496 | A1 * | 1/2014 | Sison | A61B 5/721 600/301 |
| 2014/0243696 | A1 | 8/2014 | Peyton | |
| 2020/0367861 | A1 | 11/2020 | De Wild | |
| 2021/0196228 | A1 | 7/2021 | Raju | |
| 2023/0277074 | A1 * | 9/2023 | Similä | A61B 5/02416 600/473 |

OTHER PUBLICATIONS

Moller-Sorensen et al., "Transesophageal Doppler reliably tracks changes in cardiac output in comparison with intermittent pulmonary artery thermodilution in cardiac surgery patients", J Clin Monit Comput., vol. 31, pp. 135-142, 2017. (Year: 2017).*

International Search Report Dated Aug. 8, 2023 for International Appln No. PCT/EP2023/063528 Filed May 19, 2023.

H. Hossein-Nejad, P. Mohammadinejad, A. Zeinoddini, S. Seyedhosseini Davarani, and M. Banaie, "A new modality for the estimation of corrected flow time via electrocardiogramas an alternative to Doppler ultrasonography," Ann Noninvasive Electrocardiol, vol. 23, No. 1, Jan. 2018.

Semiz Beren et al: "Non-Invasive Wearable Patch Utilizing Seismocardiography for Peri-Operative Use in Surgical Patients", IEEE J Biomed Health Inform. May 2021;25(5):1572-1582. doi: 10.1109/JBHI.2020.3032938.

Emmanuel Lorne et al: "Respiratory variations of R-wave amplitude in lead II are correlated with stroke volume variations evaluated by transesophageal Doppler echocardiography", J Cardiothorac Vasc Anesth. Jun. 2012;26(3):381-6. doi: 10.1053/j.jvca.2012.01.048.

Niederer, S.A., Sacks, M.S., Girolami, M. et al. Scaling digital twins from the artisanal to the industrial. Nat Comput Sci 1, 313-320 (2021). https://doi.org/10.1038/s43588-021-00072-5.

Baillargeon B, Rebelo N, Fox DD, Taylor RL, Kuhl E. The Living Heart Project: A robust and integrative simulator for human heart function. Eur J Mech A Solids. Nov. 2014;48:38-47. doi: 10.1016/j.euromechsol.2014.04.001. PMID: 25267880; PMCID: PMC4175454.

Jarvis L, Moninger S, Pavon J, Throckmorton C, Caves K. Accelerometer-Based Machine Learning Categorization of Body Position in Adult Populations. Comput Help People Spec Needs. 2020; 12377:242-249. Doi:10.1007/978-3-030-58805-2_29.

Aström M, García J, Laguna P, Pahlm O, Sörnmo L. Detection of body position changes using the surface electrocardiogram. Med Biol Eng Comput. Mar. 2003;41(2):164-71. Doi: 10.1007/BF02344884. PMID: 12691436.

Brigo F, Storti M, Bongiovanni LG, Fiaschi A. ECG myogenic artifacts during clonic seizures: a disturbing (and interesting) finding. J Clin Monit Comput. Apr. 2011;25(2):151-3. Doi: 10.1007/s10877-011-9279-z. Epub Apr. 22, 2011. PMID: 21512778.

Matsumoto M, Hanrath P, Kremer P, Bleifeld W. Transesophageal echocardiographic evaluation of left ventricular function at rest and during dynamic exercise in aortic insufficiency. J Cardiogr. Dec. 1981; 11(4):1147-57. PMID: 7345121.

Shin S, Mousavi A, Lyle S, Jang E, Yousefian P, Mukkamala R, Jang DG, Kwon UK, Kim YH, Hahn JO. Posture-Dependent Variability in Wrist Ballistocardiogram-Photoplethysmogram Pulse Transit Time: Implication to Cuff-Less Blood Pressure Tracking. IEEE Trans Biomed Eng. Jan. 2022;69(1):347-355. doi: 10.1109/TBME.2021.3094200. Epub Dec. 23, 2021. PMID: 34197317.

M. Takano and A. Ueno, "Noncontact In-Bed Measurements of Physiological and Behavioral Signals Using an Integrated Fabric-Sheet Sensing Scheme," in IEEE Journal of Biomedical and Health Informatics, vol. 23, No. 2, pp. 618-630, Mar. 2019, doi: 10.1109/JBHI.2018.2825020.

Schmidt C. et al: "Comparison of electrical velocimetry and transoesophageal Doppler echocardiography for measuring stroke volume and cardiac output + +Declaration of interest. This study was supported by Osypka Medical GmbH, Berlin, Germany.", British Journal of Anaesthesia, vol. 95, No. 5, Nov. 1, 2005 (Nov. 1, 2005), pp. 603-610, XP093068625, ISSN: 0007-0912, DOI: 10.1093/bja/aei224 abstract; figures 1-3.

Moller-Sorensen Hasse et al: "Transesophageal Doppler reliably tracks changes in cardiac output in comparison with intermittent pulmonary artery thermodilution in cardiac surgery patients", Journal of Clinical Monitoring and Computing, Springer Netherlands, Dordrecht, vol. 31, No. 1, Nov. 17, 2015 (Nov. 17, 2015), pp. 135-142, XP036142382, ISSN: 1387-1307, DOI: 10.1007/S10877-015-9806-4.

C. Chamos, L. Vele, M. Hamilton, and M. Cecconi, "Less invasive methods of advanced hemodynamic monitoring: principles, devices, and their role in the perioperative hemodynamic optimization," Perioper Med (Lond), vol. 2, p. 19, Sep. 2013, doi: 10.1186/2047-0525-2-19.

F. S. S. Leijten and Dutch TeleEpilepsy Consortium, "Multimodal seizure detection: A review," Epilepsia, vol. 59 Suppl 1, pp. 42-47, Jun. 2018, doi: 10.1111/epi.14047.

* cited by examiner

RELIABLIITY ASSESSMENT OF CARDIAC PARAMETER MEASUREMENTS

CROSS-REFERENCE TO PRIOR APPLICATIONS

This application is the U.S. National Phase application under 35 U.S.C. § 371 of International Application No. PCT/EP2023/063528, filed on May 19, 2023, which claims the benefit of International application Ser. No. 22/177,669.3 filed on Jun. 7, 2022. These applications are hereby incorporated by reference herein.

FIELD OF THE INVENTION

The invention relates to a method, a computer program, and a system for assessing reliability of cardiac parameter measurements of a subject, based on a trans-oesophageal echocardiography probe, a heart activity sensor and a motion sensor.

BACKGROUND OF THE INVENTION

Patients in critical care settings often need continuous monitoring of vital and cardiac parameters. Ultrasound (US) is one of the most widely used technologies for the assessment of cardiac parameters in critical care settings. In intensive care units (ICU), transthoracic cardiac assessment (Transthoracic Echocardiography-TTE) and Trans-Esophageal Echocardiography (TEE) are prevalent modes of US-based cardiac assessment. TEE is a preferred modality for assessment for cardiac surgery patients and is also used for the cases where TTE is not feasible. The advantage of TEE over TTE is that it can be used for continuous cardiac parameter monitoring, lasting for a long duration e.g., from a few minutes to a few days.

For TEE, a specialized probe containing an ultrasound transducer at its tip is used. This probe is passed into the patient's oesophagus for cardiac assessment. As the oesophagus is directly posterior to the heart, TEE provides a good visualization of the posterior structure of the heart such as the aorta, pulmonary artery, and heart valves. One disadvantage of the TEE probe is that it can get displaced due to patient's movements (physical movement, tremors, seizures etc.) or due to other procedural reasons. Next to that, TEE still remains as an operator-based manual procedure; TEE requires operator's presence near bed side for longer durations. Secondly, TEE still has a narrow field-of-view and might require continuous adjustment to keep the probe in a good position. This can be very tedious and physically challenging process and thus is prone to error during acquisitions.

Correct positioning of the TEE probe is important for continuous cardiac monitoring, as even small misalignments of the probe can lead to error in measurement. It has been recommended that a TEE Doppler beam must be within 20° of axial flow to obtain a good measure of aortic blood flow. Maintaining a proper position of the TEE probe can be challenging, especially when TEE is used for a long duration cardiac assessment. Misalignments of the probe also make it difficult to decide whether a change in a certain parameter is due to actual change in cardiac status or due to the probe's displacement.

Apart from cardiac parameters, the patients in ICU also need continuous monitoring of vital signs e.g., heart rate, blood pressure, oxygen saturation, electrocardiogram, etc. For example, electrocardiography (ECG) measures the electrical activity of the heart and can be used to derive certain cardiac parameters. Furthermore, photoplethysmography (PPG), ballistocardiography (BCG) and other techniques may also be used for deriving cardiac parameters of patients.

In a way, both US and ECG are used to measure different properties of the heart. US measures the mechanical (functional) properties, whereas ECG measures the electrical properties of the heart. Therefore, the simultaneous measurement and analysis of these two different properties can be used to get a better idea of overall cardiac status or to track changes in cardiac status. The complimentary relationship of these two modalities is well documented in literature. Utilizing this relationship, researchers have also proposed to use one modality (e.g., TEE) as an alternative to the other (e.g., ECG). In one such study, H. Hossein-Nejad, P. Mohammadinejad, A. Zeinoddini, S. Seyedhosseini Davarani, and M. Banaie, "A new modality for the estimation of corrected flow time via electrocardiography as an alternative to Doppler ultrasonography," Ann Noninvasive Electrocardiol, vol. 23, no. 1, January 2018, have demonstrated the use of ECG as an alternative to US to measure certain flow properties in the carotid artery.

Semiz Beren et al: "Non-Invasive Wearable Patch Utilizing Seismocardiography for Peri-Operative Use in Surgical Patients", IEEE J Biomed Health Inform. 2021 May; 25(5): 1572-1582. doi:10.1109/JBHI.2020.3032938, demonstrates the feasibility of a wearable patch system to monitor the SV continuously and non-invasively that is applicable to pre-, intra- and post-operative periods.

Emmanuel Lorne et al: "Respiratory variations of R-wave amplitude in lead II are correlated with stroke volume variations evaluated by transesophageal Doppler echocardiography", J Cardiothorac Vasc Anesth. 2012 June; 26(3): 381-6. doi: 10.1053/j.jvca.2012.01.048, concludes that Respiratory R-wave variations in lead II (ΔRII) is correlated with stroke volume variations as determined by transesophageal echocardiography in mechanically ventilated patients and can identify the stroke volume variation cutoff of 15%, previously determined to be the cutoff for volume responsiveness.

SUMMARY OF THE INVENTION

It is, inter alia, an object of the invention to address at least in part the problem of checking reliability of a cardiac parameter of a subject computed by a TEE probe and another sensor capable of detecting heart activity.

The invention is defined by the independent claims. Advantageous embodiments are defined in the dependent claims.

A first aspect of the invention provides a method for assessing reliability of a cardiac parameter of a subject, the method comprising:

- receiving data from a transesophageal echocardiography probe,
- receiving data from a heart activity sensor,
- receiving data from a motion sensor,
- determining a TEE cardiac parameter relating to the cardiac parameter estimated using data from the transesophageal echocardiography probe,
- determining a heart activity cardiac parameter relating to the cardiac parameter estimated using data from the heart activity sensor,
- determining the cardiac parameter based on at least one of the TEE and heart activity parameter,
- determining a cardiac parameter trend and whether the cardiac parameter trend exceeds a trend threshold, detecting motion of the subject during a first time period, based on the data of the motion sensor, assessing the reliability of the cardiac parameter based on the TEE and heart activity parameters and the data from the motion sensor, and based on whether the cardiac parameter trend exceeds the trend threshold and on whether motion of the subject has been detected, and transmitting to an output device, a feedback signal based on the reliability of the cardiac parameter.

The solution provided by the invention involves monitoring one or more cardiac parameters of a subject using a TEE probe along with a sensor capable of monitoring heart activity and a sensor capable of detecting motion. The reliability of the monitored cardiac parameter is assessed based on the signals derived from the TEE probe, the heart activity sensor and the motion sensor.

Any known TEE probe can be used, e.g., using M-mode, Doppler, two-dimensional, three-dimensional echocardiography.

According to the invention, a TEE cardiac parameter and a heart activity cardiac parameter are determined. Determining these parameters includes that either the TEE and heart activity cardiac parameters are determined, e.g., cardiac output derived from data from the TEE probe and the heart activity monitor respectively, or alternatively a TEE cardiac parameter signal relating to the TEE cardiac parameter and a heart activity cardiac parameter signal, relating to the heart activity cardiac parameter are determined, derived from the TEE probe and the heart activity probe respectively.

In order to assess the reliability of the cardiac parameter, the cardiac parameter itself needs to be determined. This is the cardiac parameter, i.e., the measurement, whose reliability the method aims to assess. In an example, the cardiac parameter is cardiac output of a subject and thus the method aims to assess if this measurement is reliable. The cardiac parameter can be determined based solely on the TEE cardiac parameter, i.e., the cardiac parameter estimated using data from the TEE probe, it can also be determined based solely on the heart activity cardiac parameter, i.e., the cardiac parameter estimated using data from the heart activity sensor, or alternatively it can be determined based on both the TEE and heart activity cardiac parameters. In the latter case the cardiac parameter can, for example, be an average or a weighted average of the TEE and heart activity cardiac parameters, or another common statistical analysis may be used.

According to the invention, the complimentary relationship between TEE and the heart activity sensor is used to check reliability of the assessment of one modality (e.g., TEE) using the other modality (e.g., heart activity sensor). Nevertheless, it would not be possible to detect errors such as probe misalignments or heart activity sensor displacements by a mere co-analysis of the TEE probe and heart activity sensor data. This is feasible, if also data from the motion sensor are taken into account. Thus, assessing reliability of the measured cardiac parameter of a subject can be achieved by utilizing data from all three the TEE probe, the heart activity sensor, and the motion sensor.

The motion sensor may be an inertial sensor (i.e., accelerometer or gyroscope), a magnetometer, an optical sensor (e.g., a camera), a radar, an electromyography (EMG) sensor, a pressure sensor, or a bed pad. In case the motion sensor is attached on the subject's body, it is preferably positioned at the subject's torso as this location may provide easier or more accurate body movement detection compared to the limbs. More preferably, the motion sensor is positioned on the chest surface of the subject above the heart, as it is a preferred area for detecting any significant movement, which can displace the TEE probe.

Alternatively, or additionally, the motion sensor may be an inertial sensor or a magnetometer included in a device comprising the heart activity sensor. For example, such a device may be a wearable biosensor for monitoring vital signs of a subject comprising the heart activity (e.g., ECG) sensor and the motion sensor. This embodiment has the advantage of simplifying workflow, as a single module having both the heart activity sensor and the motion sensor needs to be placed on the subject. Another benefit is that when the device is placed on the chest surface of the subject over the heart, this is an advantageous position to monitor any significant movement in chest area, which can lead to the displacement of the TEE probe.

The motion sensor may alternatively, or additionally be an inertial sensor or a magnetometer included in the transesophageal echocardiography probe. This arrangement could be advantageous for detecting small amplitude movements such as swallowing, which are localized and have little effect on chest wall movements.

Alternatively, or additionally, the motion sensor may be a Balistocardiograpy (BCG), Gyrocardiography (GCG), and/or seismocardiography (SCG) sensor, as motion information can be extracted from BCG, GCG, and/or SCG signals. This arrangement could be advantageous for instances when readings of an additional motion sensor are not accessible, e.g., the motion sensor is detached, not working, or data is corrupted. Another advantage is that BCG, GCG, and SCG sensors are also heart activity sensors, so they can be used as both a motion and a heart activity sensor, thereby reducing the cost and complexity of a system carrying out the method.

More than one motion sensors may be used according to the method. In this case, co-analysis of motion data from the plurality of motion sensors can be used for assessing reliability of the obtained cardiac parameters.

Assessing the reliability of the cardiac parameter means assessing whether the determined cardiac parameter is considered reliable, i.e., accurate and/or not erroneous. Assessing the reliability of the cardiac parameter may also comprise determining at least one of whether the transesophageal echocardiography probe has been misaligned, whether the heart activity sensor has been displaced, whether a cardiac parameter change has been induced by the motion of the subject, and whether the cardiac parameter change is induced by a change in cardiac status.

As mentioned above, the method also includes determining a cardiac parameter trend, determining if the cardiac parameter trend exceeds a trend threshold, detecting motion of the subject during a first time period, based on the data of the motion sensor, determining whether the cardiac parameter trend exceeds the trend threshold, and assessing the reliability of the cardiac parameter based on whether the cardiac parameter trend exceeds the trend threshold and on whether motion of the subject has been detected. These steps enable the method to provide extra information regarding cardiac parameter reliability. The cardiac parameter trend is determined, for assessing if there has been a significant change in the cardiac parameter.

The method may additionally involve comparing the TEE cardiac parameter and the heart activity cardiac parameter to detect a correlated change between them. The correlated change between the TEE cardiac parameter and the heart activity cardiac parameter signifies that the measurements of both modalities are in line with each other. For example, if the TEE cardiac parameter shows a change in cardiac output of a subject and the heart activity parameter shows a change considered in line with the TEE cardiac parameter, then the TEE and heart activity cardiac parameters are determined to be correlated. In case a correlated change has not been detected, a first signal may be transmitted to the output device. Purpose of the first signal is to communicate the inability to assess the reliability of the cardiac parameter, due to the fact that there is a difference between the cardiac parameters as determined by the different modalities which is not as expected. The signal may communicate that reliability of the cardiac parameter cannot be assessed, may also provide further information, e.g., that there is no correlation of data derived from the TEE probe and the heart activity monitor, and may also provide suggestions to the user, e.g., check whether the heart activity sensor has been displaced, or whether there is an issue hindering reception of data from the TEE probe, or the heart activity sensor.

The method may further include determining at least one of a type of the motion of the subject, wherein the type is physiological or pathological, and determining an impact of the motion of the subject on the cardiac parameter and assessing the reliability of the cardiac parameter based on the type and/or impact of the motion of the subject. Certain physical conditions such as shivering, tremors, epileptic seizures, or the subject's body movement due to position change (all of them are common in ICU patients) may also be taken into account using the motion sensor. Categorizing motion of the subject (i.e., type or impact) can enable the method to identify if or how motion can affect the reliability of the cardiac parameter.

The method may further comprise determining a TEE cardiac parameter change during a second time period, determining whether the TEE cardiac parameter change corresponds to the type and/or impact of the motion of the subject, determining a heart activity cardiac parameter change during the second time period, determining whether the heart activity cardiac parameter change corresponds to the type and/or impact of the motion of the subject, and assessing the reliability of the cardiac parameter based on whether the TEE and heart activity cardiac parameter changes correspond to the type and/or impact of the motion of the subject. These extra steps enable the method to determine at least one of the following:

- Determine that the cardiac parameter change is induced by the motion of the subject, when the TEE and the heart activity cardiac parameter changes correspond to the type and/or impact of the motion of the subject.
- Determine that the transesophageal echocardiography probe has been misaligned, when the TEE cardiac parameter change does not correspond to the type and/or impact of the motion of the subject and the heart activity cardiac parameter change corresponds to the type and/or impact of the motion of the subject.
- Determine that the electrocardiogrpahy electrode has been displaced, when the TEE cardiac parameter change corresponds to the type and/or impact of the motion of the subject and the heart activity cardiac parameter change does not correspond to the type and/or impact of the motion of the subject.

In case both the TEE and heart activity cardiac parameter changes do not correspond to the type and/or impact of the motion of the subject, the method may not be able to assess the reliability of the cardiac parameter, due to lack of adequate information. In this case the method transmits to the output device a second signal. Purpose of the second signal is to communicate the inability to assess the reliability of the cardiac parameter. The signal may communicate that reliability of the cardiac parameter cannot be assessed, may also provide further information, e.g. that the TEE and heart activity cardiac parameter changes do not correspond to the type and/or impact of the motion of the subject, and may also provide suggestions to the user, e.g. check whether the heart activity sensor or the motion sensor have been displaced or whether there is an issue hindering reception of data from the TEE probe, the heart activity sensor or the motion sensor.

The method may also comprise determining a TEE cardiac parameter change during a third time period, determining a heart activity cardiac parameter change during the third time period, determining that the cardiac parameter change is induced by a change in cardiac status, when the motion of the subject does not exceed a motion threshold during the first time period, and the TEE cardiac parameter change correlates with the heart activity cardiac parameter change, or transmitting to the output device a third signal when the motion of the subject does not exceed the motion threshold during the first time period, and the TEE cardiac parameter change does not correlate with the heart activity cardiac parameter change. This embodiment concerns the option to assess cardiac parameter reliability when motion of the subject is considered low, absent, or of low consequence. In this case, the method can either determine that the cardiac parameter measurement is reliable, or that reliability cannot be assessed. When reliability cannot be assessed, a third signal is transmitted to the output device. Similarly, to the first and second signals, purpose of the third signal is to communicate the inability to assess the reliability of the cardiac parameter. The signal may communicate that reliability of the cardiac parameter cannot be assessed, may also provide further information, e.g., that the TEE cardiac parameter change does not correlate with the heart activity cardiac parameter change, and may also provide suggestions to the user, e.g., check whether the heart activity sensor or the motion sensor have been displaced or whether there is an issue hindering reception of data from the TEE probe, the heart activity sensor or the motion sensor.

In another aspect of the invention, a computer program for assessing reliability of a cardiac parameter of a subject is provided, enabling a processor to carry out the method as described herein.

In another aspect of the invention, a system for assessing reliability of a cardiac parameter of a subject is provided, the system comprising: a transesophageal echocardiography probe, a heart activity sensor, a motion sensor configured to detect motion of the subject, an output device, and a processor configured to carry out the method as described herein.

The advantages and technical effects as already described for the method also apply to the corresponding computer program and system.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DESCRIPTION OF EMBODIMENTS

Figure 1:
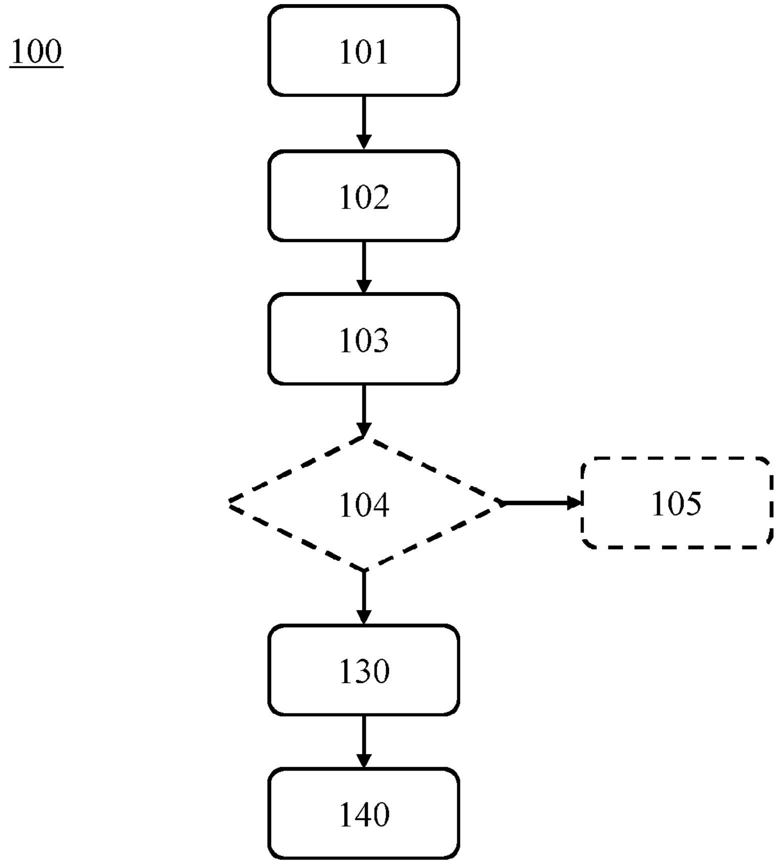
FIG. 1 shows a flowchart of a method for assessing reliability of a cardiac parameter of a subject according to an example.

The invention will be described with reference to the Figures. The detailed description and specific examples, while indicating exemplary embodiments of the invention, are intended for purposes of illustration only and are not intended to limit the scope of the invention. These and other features, aspects, and advantages of the present invention will become better understood from the following description, appended claims, and accompanying drawings. The Figures are merely schematic and are not drawn to scale. It should also be understood that the same reference numerals are used throughout the Figures to indicate the same or similar parts.

According to an example, the invention provides a method 100 for assessing reliability of a cardiac parameter of a subject using a TEE (transesophageal echocardiography) probe, a heart activity sensor, and a motion sensor. FIG. 1 shows a flowchart of this method 100. In a first step 101, the method comprises receiving data from the TEE probe, the heart activity sensor, and the motion sensor.

The TEE probe is positioned accordingly in the subject. The heart activity sensor may be any sensor capable of sensing heart activity, e.g., a photoplethysmography (PPG), camera, acoustic, ultrasound, electrocardiography (ECG), ballistocardiography (BCG), Gyrocardiography (GCG), or a seismocardiography (SCG) sensor. Preferably, the heart activity sensor is either ECG or a BCG sensor, as these sensors can be used to estimate a broad range of cardiac parameters and can also provide reliable measurements in continuous heart monitoring. Furthermore, more than one heart activity sensors may be used, such as a combination of ECG, BCG with any of a PPG, camera, acoustic or ultrasound sensor.

The determined cardiac parameters may be at least one of cardiac output, stroke volume, left-ventricular filling pressure, ejection fraction, blood flow, heart rate, heart rhythm, heart rate variability, left- and right-ventricular volume, left- and right-atrial volume, pulmonary artery pressure. Preferably, the determined parameters are at least one of cardiac output, heart rate, heart rhythm, and heart rate variability. All the aforementioned parameters can be determined or derived using the TEE probe and ECG. Most of these parameters can also be measured directly or indirectly using BCG. Other heart activity sensors may not be able to determine all the mentioned cardiac parameters and the determination of the cardiac parameter whose reliability is assessed by the method, thus depends on the heart activity sensor to be used. A person skilled in this area is familiar with which cardiac parameters can be determined by each heart activity sensor.

In one example, the method is used for assessing reliability of a cardiac parameter of a subject monitored continuously. Continuous monitoring of cardiac parameters is preferred or needed for subjects in certain wards in hospitals, e.g., in ICUs. In one example, the method can be used for assessing reliability of cardiac output (CO) measurements, over a period of time lasting from a few minutes to a few hours or days.

In step 102, a TEE cardiac parameter and a heart activity cardiac parameter are determined. The TEE cardiac parameter relates to the cardiac parameter determined by using the TEE probe. The TEE cardiac parameter can thus be the cardiac parameter as determined by using the TEE probe, or alternatively a TEE cardiac parameter signal which relates to the TEE cardiac parameter, i.e., a signal which when processed provides the cardiac parameter. Similarly, the heart activity cardiac parameter relates to the cardiac parameter determined by using the heart activity sensor. The heart activity cardiac parameter can thus be the cardiac parameter as determined by using the heart activity sensor, or alternatively a heart activity cardiac parameter signal which relates to the heart activity cardiac parameter, i.e., a signal which when processed provides the cardiac parameter. Both the TEE and the heart activity cardiac parameters relate to the same cardiac parameter, e.g., cardiac output, heart rate, heart rhythm, heart rate variability, stroke volume, left-ventricular filling pressure, ejection fraction, etc.

In step 103, the cardiac parameter to be assessed is determined. In one embodiment, the measurement of the cardiac parameter is based solely on the TEE cardiac parameter, i.e., the cardiac parameter to be assessed is measured using the TEE probe. In another embodiment, the measurement of the cardiac parameter is based solely on the heart activity cardiac parameter, i.e., the cardiac parameter to be assessed is measured using the heart activity sensor. In a third embodiment the measurement of the cardiac parameter is based on both the TEE and heart activity cardiac parameters.

In an example, the method comprises the step 104 of comparing the TEE cardiac parameter with the heart activity cardiac parameter, for detecting expected correlated changes or discrepancies between them. Determining whether the changes are correlated may be achieved by using any suitable statistical analysis, as for example disclosed by the above-mentioned article from Hossein-Nejad et al. (2018).

In case no correlation between the TEE cardiac parameter and the heart activity cardiac parameter is established, in an optional step 105, a first signal is transmitted, communicating the inability to assess the reliability of the cardiac parameter.

Having determined the cardiac parameter in step 103, in step 130, its reliability is assessed. In this step, the TEE cardiac parameter and the heart activity cardiac parameter, already determined in step 102, and data from the motion sensor are used for assessing the reliability of the cardiac parameter.

There are different options for determining the cardiac parameter reliability in step 130. In an example, rules are defined using the TEE cardiac parameter, the heart activity cardiac parameter and data from the motion sensor. Such rules can be defined by the user or can be imported from user-annotated historical data. For instance, such a rule could be that if data from the motion sensor show absence of any significant movement, the TEE cardiac parameter and heart activity parameter will be considered reliable, thus the determined cardiac parameter is reliable as well. Another rule is that, if significant motion is detected, followed by a change in cardiac parameters, which is proportional to the detected motion and lasts only for the time expected due to motion, then the determined cardiac parameter will also be considered reliable.

Additionally, or alternatively, for determining the cardiac parameter in step 130 annotated vectors can be used to train a machine learning classifier. In this case, the measurement input vectors include TEE, heart activity, and motion data, and each vector is annotated by users in terms of reliability. In case of binary classification, one can use "reliable" and "non-reliable" labels. Using the annotated vectors, a classifier can be trained. Example methods to use are neural networks, support vector machines, decision trees, naïve bayes, logistic regression, etc. For training the machine learning classifier, collected past data can be used. Once the classifier is trained, it can receive as input TEE, heart activity and motion data and then generate an output indicating the reliability of these measurements.

Additionally, or alternatively, a physiological digital twin of the heart, or the cardiovascular system can be used to run simulations as for example explained in: Niederer, S. A., Sacks, M. S., Girolami, M. et al. Scaling digital twins from the artisanal to the industrial. Nat Comput Sci 1, 313-320 (2021). https://doi.org/10.1038/s43588-021-00072-5 and Baillargeon B, Rebelo N, Fox D D, Taylor R L, Kuhl E. The Living Heart Project: A robust and integrative simulator for human heart function. Eur J Mech A Solids. 2014 November; 48:38-47. doi: 10.1016/j.euromechsol.2014.04.001. PMID: 25267880; PMCID: PMC4175454. Using the measured TEE, heart activity and motion data as input to the digital twin, reliability of the cardiac parameter can be determined. The digital twin can be considered as a validated copy of the physical object and using the digital twin different signal and parameters can be synthesized. In an example, a synthesizer can be used with the digital twin, where two signals e.g., the TEE cardiac parameter and data from the motion sensor will be used as input, and a simulated signal, e.g., a simulated heart activity parameter will be generated by the digital twin. The simulated signal, e.g., the simulated heart activity parameter can then be compared with the measured signal, e.g., the measured heart activity parameter and if there are discrepancies between the simulated and the measured signal, then it is assessed that the cardiac parameter is not reliable. Due to the motion sensor data, the type and timing of the artifacts expected in the TEE and heart activity cardiac parameters can also be estimated using the digital twin, which can then be compared with the measured ones. If they are found to be different, it can be concluded that any one of the TEE cardiac parameter, heart activity parameter or motion data are not reliable, thus the determined cardiac parameter is not reliable.

Additionally, or alternatively, in step 104, the TEE cardiac parameter is compared to the heart activity cardiac parameter to detect a correlated change between them and the assessment of reliability of the cardiac parameter is based on whether a correlated change and motion of the subject has been detected. If data from the motion sensor shows no or insignificant motion of the subject, and the TEE cardiac parameter is in line with the heart activity cardiac parameter, then the cardiac parameter is deemed to be reliable. If data from the motion sensor shows significant motion of the subject, and the TEE cardiac parameter is not in line with the heart activity cardiac parameter, then reliability of the cardiac parameter cannot be determined. For example, if the TEE cardiac parameter and the heart activity parameter values differ less than +/−5%, then they are considered to be in line with each other. A digital twin can also be used, by simulating the digital twin with patient data or representative input settings to generate simulated TEE and heart activity parameters. A correlation between the simulated TEE and heart activity parameter can then be computed. The computed correlation can then be compared to a correlation between the measured TEE and heart activity parameter. For example, if the correlation between the simulated and the measured parameters differs and the motion sensor shows no or insignificant motion of the subject, then it can be concluded that the determined cardiac parameter is not reliable. Furthermore, if the correlation between the simulated and the measured parameters does not differ then it can be concluded that the determined cardiac parameter is reliable.

In one embodiment, data gathered from the TEE probe, the heart activity sensor, and the motion sensor may be synchronized.

Assessing the reliability of the cardiac parameter involves one or more of the following: determining that the cardiac parameter is or is not considered reliable, determining whether the TEE probe has been misaligned, determining whether the heart activity sensor has been displaced, determining whether a cardiac parameter change has been induced by the motion of the subject, and determining whether the cardiac parameter change is induced by a change in cardiac status. There is also the case that reliability as defined above cannot be determined.

Not all of the above options for assessing cardiac parameter reliability need be determined by the method. In one embodiment, the method may only be able to determine that the cardiac parameter is considered reliable, in another embodiment may only be able to determine if the TEE probe has been misaligned, and in another embodiment whether the heart activity sensor has been displaced and so forth. In a further embodiment, the method may be able to determine all of the above.

In step 140, after having assessed the reliability of the cardiac parameter, a feedback signal is transmitted to an output device based on the reliability of the cardiac parameter. The output device may be a screen, a handheld device such as a tablet, an indicator light, a database, or a speaker. For example, in various embodiments the feedback signal may involve communicating that the cardiac parameter measurement is or is not considered reliable, the TEE probe has been misaligned, that the heart activity sensor has been displaced, that the cardiac parameter change has been induced by motion of the subject, that the cardiac parameter change was induced by a change in cardiac status, or that reliability cannot be determined. In another embodiment the feedback signal may also transmit the measured cardiac parameter. In this case the transmitted cardiac parameter may be the cardiac parameter as determined only by the TEE probe, only by the heart activity sensor, or determined by combining the TEE probe and heart activity sensor signals. In yet another embodiment the feedback signal may also transmit the TEE cardiac parameter and/or the heart activity cardiac parameter.

Figure 2:
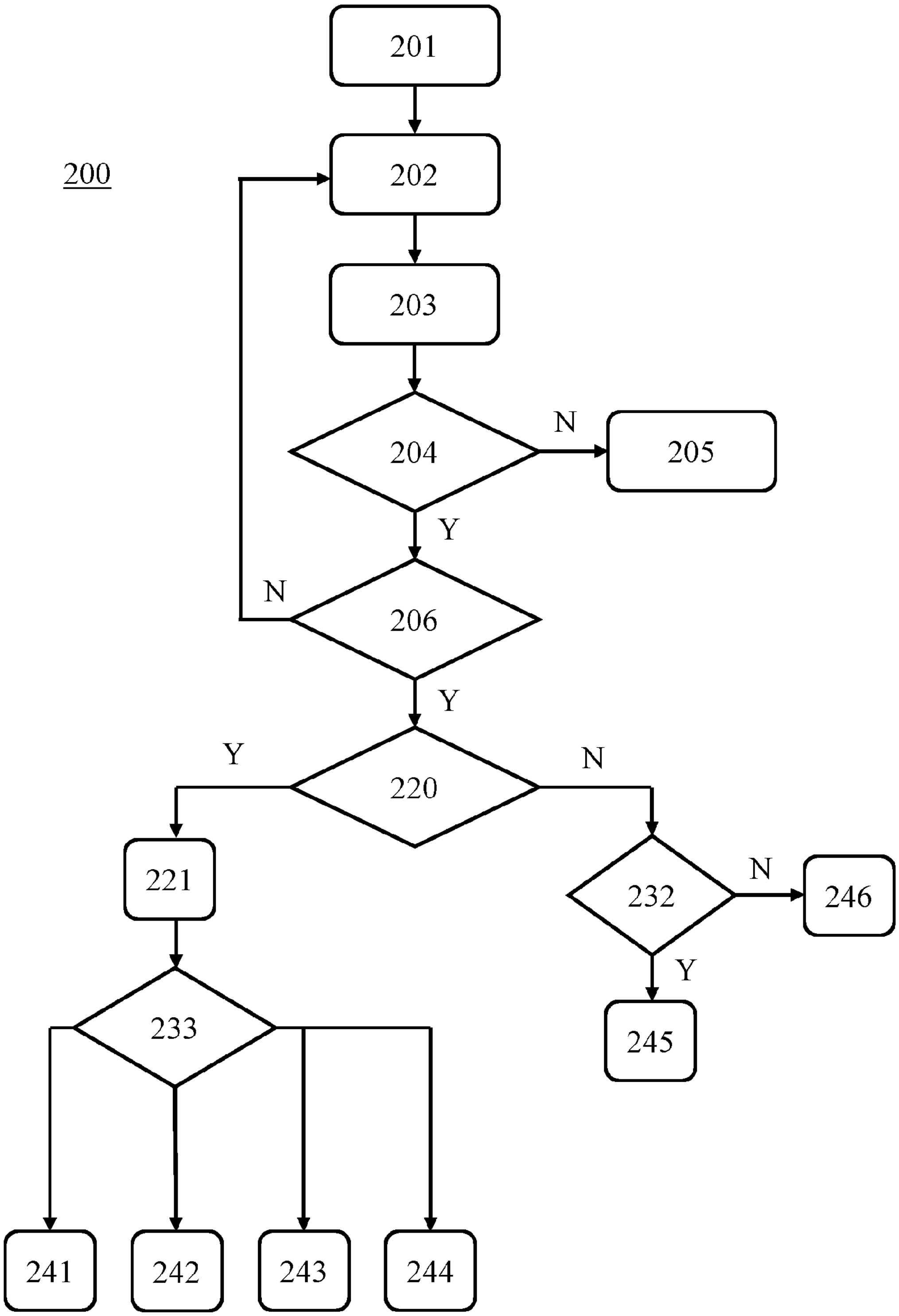
FIG. 2 shows a flowchart of a method for assessing reliability of a cardiac parameter of a subject according to an embodiment.

FIG. 2 depicts a flowchart of method 200. Steps 201-205 correspond to steps 101-105 of the already described method 100, and for the sake of conciseness these steps will not be described again.

In step 206, a trend of the cardiac parameter is determined. The trend can be determined according to known trend analysis methods. The cardiac parameter trend is determined in order to assess whether any significant change in the cardiac parameter has occurred. It is then checked whether the cardiac parameter trend exceeds a trend threshold. For this purpose, thresholds as defined in literature or empirical thresholds can be used. For example, a change of 10% over the initial or a baseline cardiac parameter can be used for determining the trend threshold. The trend threshold may not be constant as the initial or baseline cardiac parameter may also not be constant. For example, if the cardiac parameter has changed in a previous measurement, the cardiac parameter of the previous measurement may be used as a baseline cardiac parameter for calculating the trend threshold for the following cardiac parameter trend assessment.

In case the cardiac parameter trend does not exceed the trend threshold value, then the method may return to step 202 where the TEE cardiac parameter and the heart activity cardiac parameter are determined. In case the trend of the cardiac parameter exceeds the threshold value, the method proceeds to step 220.

In step 220, the subject's body movement data is checked to detect motion of the subject within a first time period T1. This first time period may have a duration of a few seconds, e.g., 1-10 seconds, and preferably 1-5 seconds, before a change in the cardiac parameter occurred. In one example the first time period has a starting point of a few seconds before the cardiac parameter trend exceeds the trend threshold in the first instance, taking into account that a cardiac parameter may exceed the trend threshold multiple times after a significant motion.

Use of motion sensors for detecting body motion is well established in the literature, e.g., in: Jarvis L, Moninger S, Pavon J, Throckmorton C, Caves K. Accelerometer-Based Machine Learning Categorization of Body Position in Adult Populations. Comput Help People Spec Needs. 2020; 12377:242-249. Doi:10.1007/978-3-030-58805-2_29. Using established processing methods, motion sensor data is processed to detect body movement in the first time period. For example, if detected motion of the subject does not exceed a motion threshold, e.g., 10% change in motion data over initial/baseline motion data, then it is determined that no motion or no significant motion has occurred. Additionally, or alternatively, if detected motion of the subject does not exceed a change in angle up to 15 degrees, e.g., in angle up to 10 degrees over the initial orientation of the subject detected by the sensor in any axis, then it is determined that no motion or no significant motion has occurred.

Reliability of the cardiac parameter can then be assessed, taking into account whether the cardiac parameter trend has exceeded the trend threshold, and whether motion of the subject has been detected. In case the cardiac parameter trend does not exceed the trend threshold, the method may not proceed in determining cardiac parameter reliability, until a change has happened. If the cardiac parameter trend exceeds the trend threshold, therefore a significant change in the cardiac parameter has occurred, it is then checked whether this change has occurred while the subject moved. In one example, if no significant motion is determined, if the TEE cardiac parameter is in line with the heart activity cardiac parameter and the cardiac parameter trend exceeds the trend threshold, it can be determined that the cardiac parameter change is induced by a change in cardiac status. In another example, if motion is determined, if the TEE cardiac parameter is not in line with the heart activity cardiac parameter and the cardiac parameter trend exceeds the trend threshold, then reliability of the cardiac parameter cannot be determined.

Different types of body motion are likely to have different effects on cardiac parameters. Therefore, in optional step 221, the body motion is categorized. Body motion can be categorized into two broad types: physiological body motion, e.g., laying, reclining, sitting, standing, walking and pathological body motion, e.g., shivering, tremors, epileptic seizures. Physiological body motion usually has a transient, predictable and small effect on the measured cardiac parameters, whereas pathological body motion can significantly derange or obscure cardiac parameters. Based on information from literature or empirical data about TEE and heart activity sensor patterns and changes in different body movement, it is possible to build a database/lookup table to link body motion with expected changes derived by the TEE probe and the heart activity sensor. Examples from literature where such information may be derived are: Aström M, García J, Laguna P, Pahlm O, Sömnmo L. Detection of body position changes using the surface electrocardiogram. Med Biol Eng Comput. 2003 March; 41(2):164-71. Doi: 10.1007/BF02344884. PMID:12691436, Brigo F, Storti M, Bongiovanni L G, Fiaschi A. ECG myogenic artifacts during clonic seizures: a disturbing (and interesting) finding. J Clin Monit Comput. 2011 April; 25(2):151-3. Doi: 10.1007/s10877-011-9279-z. Epub 2011 Apr. 22. PMID: 21512778, Matsumoto M, Hanrath P, Kremer P, Bleifeld W. Transesophageal echocardiographic evaluation of left ventricular function at rest and during dynamic exercise in aortic insufficiency. J Cardiogr. 1981 December; 11(4):1147-57. PMID: 7345121, Shin S, Mousavi A, Lyle S, Jang E, Yousefian P, Mukkamala R, Jang D G, Kwon U K, Kim Y H, Hahn J O. Posture-Dependent Variability in Wrist Ballistocardiogram-Photoplethysmogram Pulse Transit Time: Implication to Cuff-Less Blood Pressure Tracking. IEEE Trans Biomed Eng. 2022 January; 69(1):347-355. doi: 10.1109/TBME.2021.3094200. Epub 2021 Dec. 23. PMID: 34197317, M. Takano and A. Ueno, "Noncontact In-Bed Measurements of Physiological and Behavioral Signals Using an Integrated Fabric-Sheet Sensing Scheme," in IEEE Journal of Biomedical and Health Informatics, vol. 23, no. 2, pp. 618-630, March 2019, doi: 10.1109/JBHI.2018.2825020.

Additionally, or alternatively, the subject's body motion can be categorized based on the expected impact of the motion on cardiac parameters. For example, body motion can be classified into three categories: (1) Low cardiac impact motion, e.g., swallowing; (2) Moderate cardiac impact motion, e.g., change position from sitting to lying; (3) high cardiac impact motion, e.g., seizures.

Additionally, or alternatively, machine learning-based methods and an annotated dataset can be used, to associate different types of body motion with an expected change in TEE and heart activity sensor cardiac parameters, and/or their raw signals.

In step 233, it is checked whether a change in the TEE cardiac parameter and a change in the heart activity cardiac parameter correspond to the type or impact of the motion of the subject. Namely it is checked whether such changes were expected in view of the type or impact of the motion of the subject as determined in step 221. For this reason, a change in the TEE cardiac parameter is determined for a second time period T2 and then it is assessed whether the TEE cardiac parameter change corresponds to the determined type or impact of the motion of the subject. The second time period T2 is calculated as the first time period T1 plus a few seconds. For example, the second time period T2 may be T1+(1 to 30) seconds, preferably T1+(1 to 10) seconds and more preferably T1+(2 to 4) seconds.

In step 233 a change in the heart activity cardiac parameter is also determined during the second time period T2. Then it is assessed whether the heart activity cardiac parameter change corresponds to the determined type or impact of the motion of the subject.

In case both the TEE and heart activity cardiac parameter changes correspond to the type or impact of the motion of the subject, in step 241 it is determined that the cardiac parameter change is induced by the motion of the subject, indicating that the obtained cardiac parameters reliably reflect change in cardiac status due to motion. A feedback signal based on this result is then transmitted to the output device.

In case the TEE cardiac parameter change does not correspond to the determined type or impact of the motion of the subject, but the heart activity cardiac parameter change does correspond to the determined type or impact of the motion of the subject, in step 242 it is determined that the TEE probe has been misaligned. A feedback signal based on this result is then transmitted to the output device.

In case the TEE cardiac parameter change corresponds to the determined type or impact of the motion of the subject, but the heart activity cardiac parameter change does not correspond to the determined type or impact of the motion of the subject, in step 243 it is determined that the heart activity sensor has been displaced. For example, depending on what kind of heart activity sensor is used, it may be determined that the ECG, PPG, BCG or EMG sensor has been misplaced. A feedback signal based on this result is then transmitted to the output device.

In case neither the TEE nor the heart activity cardiac parameter change correspond to the determined type or impact of the motion of the subject, reliability of the cardiac parameter cannot be assessed. In this case, in step 244 a second signal is transmitted to the output device, communicating the inability to assess the cardiac parameter reliability.

Step 232 may follow step 220 where the subject's body movement data has been checked and the result was that no motion or no significant motion of the subject within a first time period T1 was detected. In step 232, a TEE cardiac parameter change is determined for a third time period T3, similarly to step 233. The third time period T3 is calculated as the first time period T1 plus a number of seconds. For example, the third time period T3 may be T1+(1 to 100) seconds, preferably T1+(1 to 30) seconds and more preferably T1+(1 to 10) seconds. In step 232, a heart activity cardiac parameter change is also determined, similarly to step 233.

Afterwards, it is determined whether there is a correlation between the TEE and the heart activity cardiac parameter changes. Purpose of this correlation is to detect whether the cardiac parameter changes as detected by the TEE probe and the heart activity sensor are in line with each other. Determining whether the changes are correlated may be achieved by using any suitable statistical analysis, as for example disclosed by Hossein-Nejad et al. (2018). In an example, if the TEE cardiac parameter has changed, e.g., increased or decreased by 10%, and the heart activity cardiac parameter had a similar type of change, e.g. if the TEE cardiac parameter increased then the heart activity parameter also increased and changed by 10%, or changed by 9% to 11%, or changed by 8% to 12%, then it is considered that the TEE cardiac parameter correlates with the heart activity cardiac parameter.

If the TEE and the heart activity cardiac parameter changes are evaluated to be correlated, then in step 245 it is determined that there is a change in the cardiac status of the subject and that the measured cardiac parameter is reliable. This result is then transmitted to the output device.

On the other hand, in case the TEE cardiac parameter does not correlate with the heart activity cardiac parameter, reliability of the cardiac parameter cannot be assessed and in this case in step 246, a third signal relating to this result is transmitted to the output device.

In a second aspect of the invention, a computer program for assessing reliability of a cardiac parameter of a subject, enabling a processor to carry out the method as described herein is proposed.

The computer program may be stored/distributed on a suitable non-transitory computer-readable medium, such as an optical storage medium or a solid-state medium supplied together with or as part of other hardware, but may also be distributed in other forms, such as via the internet or other wired or wireless telecommunication systems.

Figure 3:
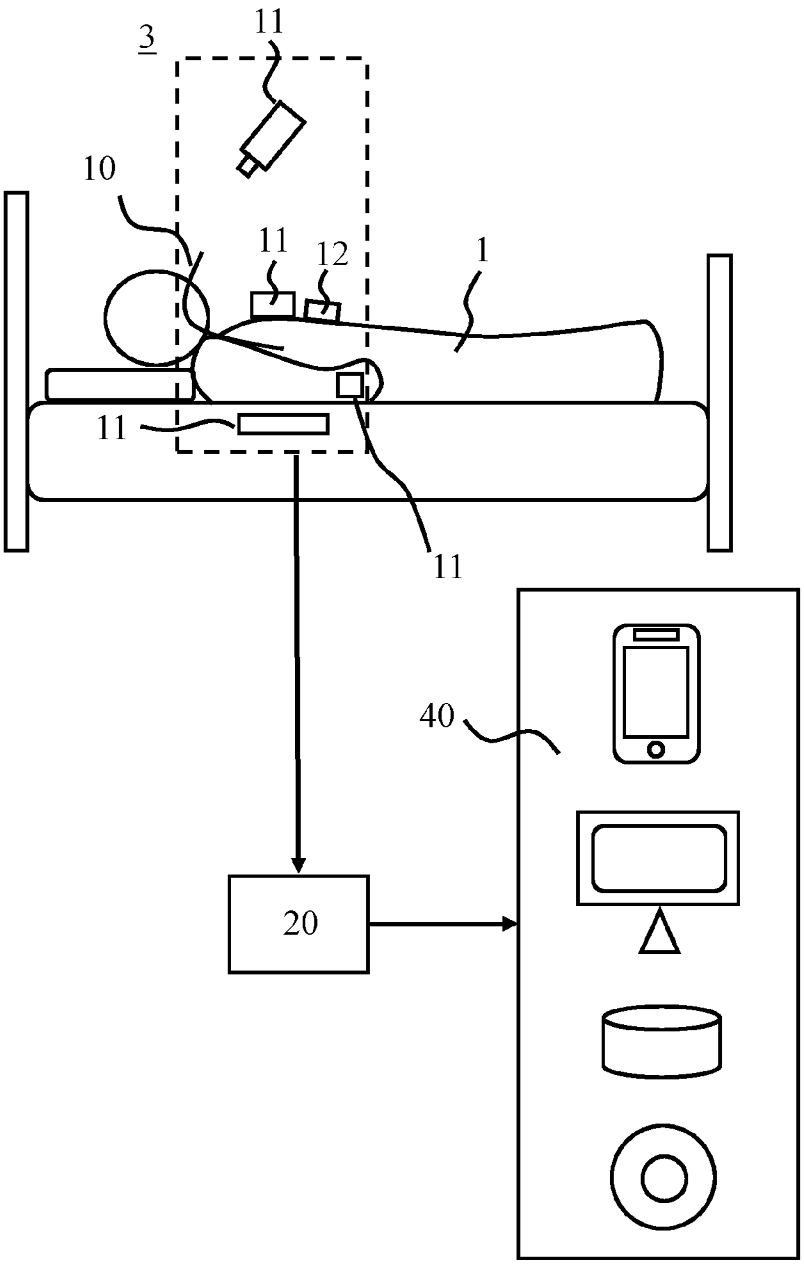
FIG. 3 schematically depicts a system for assessing reliability of cardiac parameter measurements of a subject according to an embodiment.

FIG. 3 schematically depicts an arrangement for assessing reliability of a cardiac parameter of a subject 1 by a system 3. The system 3 typically comprises a TEE probe 10, a heart activity sensor 11 and a motion sensor 12. The heart activity sensor 11 may be an electrocardiography (ECG), photoplethysmography (PPG), camera, acoustic, ultrasound, or ballistocardiography (BCG) sensor. More than one heart activity sensors may be used, such as a combination of ECG, BCG with any of a PPG, camera, acoustic or ultrasound sensor.

The motion sensor 12 may be an inertial sensor (e.g., accelerometer or a gyroscope), a magnetometer, an optical sensor (e.g., a camera), a radar, an EMG sensor, a BCG sensor, a GCG sensor, a SCG sensor, a pressure sensor, or a bed pad. In FIG. 3 the motion sensor 12 is shown to be positioned on the chest surface of the subject. Nevertheless, it may be placed at any suitable place where it can detect motion of the subject, or in case of a camera or a radar it may not be placed on the subject. Additionally, or alternatively the motion sensor 12 and the heart activity sensor 11 may be housed in the same device. For example, a device comprising the heart activity sensor, e.g., an ECG sensor and the motion sensor, e.g., an inertial sensor is attached on the subject and this device is capable of collecting data for both the heart activity and the motion of the subject. Additionally, or alternatively the TEE probe 10 may comprise one or more motion sensors 12.

The TEE probe 10, the heart activity sensor 11 and the motion sensor 12 collect data which are communicated using a wired and/or wireless interface to a processor 20. The processor 20 may comprise one or more processing elements such as one or more processors, processor cores and the like, arranged to process the data provided by the TEE probe 10, the heart activity sensor 11 and the motion sensor 12.

The TEE probe 10 and the heart activity sensor 11 are typically arranged to provide the processor 20 with signals relating to a cardiac parameter of the subject. Furthermore, the motion sensor 12 is arranged to provide the processor 20 with data relating to the motion of the subject. The processor 20 having received the signals from the TEE probe 10, the heart activity sensor 11 and the motion sensor 12 then processes these data according to the method as it has been described herein. The processor 20 then determines a cardiac parameter derived from the TEE probe 10 and/or the heart activity sensor 11 and also assesses the reliability of the determined cardiac parameter.

The processor 20 transmits, wired or wirelessly, to an output device 40, a feedback signal based on the reliability of the cardiac parameter. The output device 40 may be one or more of a monitor, a handheld device (e.g. smartphone), a database, and a speaker. The signal transmitted from the processor 20 is such that it is compatible with the signals that the output device is able to receive. For example, the processor sends a video signal to a monitor and/or an audio signal to a speaker.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor. In the device claim enumerating several means, several of these means may be embodied by one and the same item of hardware. Measures recited in mutually different dependent claims may advantageously be used in combination.

The invention claimed is:

1. A computer-implemented method for assessing reliability of a cardiac parameter of a subject, the method comprising:

receiving data from a transesophageal echocardiography (TEE) probe, receiving data from a heart activity sensor, receiving data from a motion sensor, determining a TEE cardiac parameter relating to a first estimate of a cardiac parameter obtained using data from the transesophageal echocardiography probe, determining a heart activity cardiac parameter relating to a second estimate of the cardiac parameter obtained using data from the heart activity sensor, determining the cardiac parameter based on at least one of the TEE cardiac parameter or the heart activity cardiac parameter, detecting motion of the subject during a first time period, based on the data of the motion sensor, determining at least one of a type of the motion of the subject, wherein the type is physiological or pathological, or an impact of the motion of the subject on the cardiac parameter, assessing the reliability of the cardiac parameter based on whether a TEE cardiac parameter change and a heart activity cardiac parameter change correspond to the type and/or impact of the motion of the subject, determining that the transesophageal echocardiography probe has been misaligned, when the TEE cardiac parameter change does not correspond to the type and/or impact of the motion of the subject and the heart activity cardiac parameter change corresponds to the type and/or impact of the motion of the subject, and transmitting, to an output device, a feedback signal based on the reliability of the cardiac parameter.

2. The method according to claim 1, wherein the method further comprises:

comparing the TEE cardiac parameter and the heart activity cardiac parameter to detect a correlated change between them, and transmitting to the output device a first signal if the correlated change has not been detected.

3. The method according to claim 1, wherein assessing the reliability of the cardiac parameter comprises determining at least one of whether the transesophageal echocardiography probe has been misaligned, whether the heart activity sensor has been displaced, whether a cardiac parameter change has been induced by the motion of the subject, whether the cardiac parameter change is induced by a change in cardiac status, or that the cardiac parameter is considered reliable.

4. The method according to claim 1, wherein the method further comprises:

determining the TEE cardiac parameter change during a second time period, determining whether the TEE cardiac parameter change corresponds to the type and/or impact of the motion of the subject, determining the heart activity cardiac parameter change during the second time period, and determining whether the heart activity cardiac parameter change corresponds to the type and/or impact of the motion of the subject.

5. The method according to claim 1, wherein the method further comprises:

determining that a cardiac parameter change is induced by the motion of the subject, when the TEE cardiac parameter change and the heart activity cardiac parameter change correspond to the type and/or impact of the motion of the subject.

6. The method according to claim 1, wherein the method further comprises:

determining that the heart activity sensor has been displaced, when the TEE cardiac parameter change corresponds to the type and/or impact of the motion of the subject and the heart activity cardiac parameter change does not correspond to the type and/or impact of the motion of the subject.

7. The method according to claim 1, wherein the method further comprises:

transmitting to the output device a second signal when the TEE cardiac parameter change and the heart activity cardiac parameter change do not correspond to the type and/or impact of the motion of the subject.

8. The method according to claim 1, wherein the method further comprises at least one of:

determining the TEE cardiac parameter change during a third time period, determining the heart activity cardiac parameter change during the third time period, determining that a cardiac parameter change is induced by a change in cardiac status, when the motion of the subject does not exceed a motion threshold during the first time period, and the TEE cardiac parameter change correlates with the heart activity cardiac parameter change, or transmitting to the output device a third signal when the motion of the subject does not exceed the motion threshold during the first time period, and the TEE cardiac parameter change does not correlate with the heart activity cardiac parameter change.

9. The method according to claim 1, wherein the motion sensor is at least one of:

an inertial sensor, a magnetometer, an optical sensor, a radar, an electromyography sensor, a pressure sensor, or a bed pad, an inertial sensor, or a magnetometer included in a device comprising the heart activity sensor, an inertial sensor, or a magnetometer included in the transesophageal echocardiography probe, or a balistocardiograpy, gyrocardiography, or seismocardiography sensor.

10. A non-transitory computer-readable medium that stores therein a computer program product for assessing reliability of a cardiac parameter of a subject, which, when executed by a processor, causes the processor to perform operations comprising:

receiving data from a transesophageal echocardiography (TEE) probe, receiving data from a heart activity sensor, receiving data from a motion sensor, determining a TEE cardiac parameter relating to a first estimate of a cardiac parameter obtained using data from the transesophageal echocardiography probe, determining a heart activity cardiac parameter relating to a second estimate of the cardiac parameter obtained using data from the heart activity sensor, determining the cardiac parameter based on at least one of the TEE cardiac parameter or the heart activity cardiac parameter, detecting motion of the subject during a first time period, based on the data of the motion sensor, determining at least one of a type of the motion of the subject, wherein the type is physiological or pathological, or an impact of the motion of the subject on the cardiac parameter, assessing the reliability of the cardiac parameter based on whether a TEE cardiac parameter change and a heart activity cardiac parameter change correspond to the type and/or impact of the motion of the subject, determining that the transesophageal echocardiography probe has been misaligned, when the TEE cardiac parameter change does not correspond to the type and/or impact of the motion of the subject and the heart activity cardiac parameter change corresponds to the type and/or impact of the motion of the subject, and transmitting, to an output device, a feedback signal based on the reliability of the cardiac parameter.

11. The non-transitory computer-readable medium according to claim 10, wherein the computer program product, when executed, causes the processor to perform further operations comprising:

comparing the TEE cardiac parameter and the heart activity cardiac parameter to detect a correlated change between them, and transmitting to the output device a first signal if the correlated change has not been detected.

12. The non-transitory computer-readable medium according to claim 10, wherein the computer program product, when executed, causes the processor to perform further operations comprising:

determining that the heart activity sensor has been displaced, when the TEE cardiac parameter change corresponds to the type and/or impact of the motion of the subject and the heart activity cardiac parameter change does not correspond to the type and/or impact of the motion of the subject.

13. The non-transitory computer-readable medium according to claim 10, wherein the computer program product, when executed, causes the processor to perform further operations comprising:

transmitting to the output device a second signal when the TEE cardiac parameter change and the heart activity cardiac parameter change do not correspond to the type and/or impact of the motion of the subject.

14. The non-transitory computer-readable medium according to claim 10, wherein the computer program product, when executed, causes the processor to perform further operations comprising at least one of:

determining the TEE cardiac parameter change during a third time period, determining the heart activity cardiac parameter change during the third time period, determining that a cardiac parameter change is induced by a change in cardiac status, when the motion of the subject does not exceed a motion threshold during the first time period, and the TEE cardiac parameter change correlates with the heart activity cardiac parameter change, or transmitting to the output device a third signal when the motion of the subject does not exceed the motion threshold during the first time period, and the TEE cardiac parameter change does not correlate with the heart activity cardiac parameter change.

15. A system for assessing reliability of a cardiac parameter of a subject, the system comprising:

a transesophageal echocardiography (TEE) probe, a heart activity sensor, a motion sensor configured to detect motion of the subject, an output device, a processor, and a non-transitory computer-readable medium that stores therein a computer program product which, when executed by the processor, causes the processor to perform operations comprising:

receiving data from the TEE probe, receiving data from the heart activity sensor, receiving data from the motion sensor, determining a TEE cardiac parameter relating to a first estimate of a cardiac parameter obtained using data from the transesophageal echocardiography probe, determining a heart activity cardiac parameter relating to a second estimate of the cardiac parameter obtained using data from the heart activity sensor, determining the cardiac parameter based on at least one of the TEE cardiac parameter or the heart activity cardiac parameter, detecting motion of the subject during a first time period, based on the data of the motion sensor, determining at least one of a type of the motion of the subject, wherein the type is physiological or pathological, or an impact of the motion of the subject on the cardiac parameter, assessing the reliability of the cardiac parameter based on whether a TEE cardiac parameter change and a heart activity cardiac parameter change correspond to the type and/or impact of the motion of the subject, determining that the transesophageal echocardiography probe has been misaligned, when the TEE cardiac parameter change does not correspond to the type and/or impact of the motion of the subject and the heart activity cardiac parameter change corresponds to the type and/or impact of the motion of the subject, and transmitting, to an output device, a feedback signal based on the reliability of the cardiac parameter.

16. The system according to claim 15, wherein the computer program product, when executed, causes the processor to perform further operations comprising:

comparing the TEE cardiac parameter and the heart activity cardiac parameter to detect a correlated change between them, and transmitting to the output device a first signal if the correlated change has not been detected.

17. The system according to claim 15, wherein the computer program product, when executed, causes the processor to perform further operations comprising:

determining that the heart activity sensor has been displaced, when the TEE cardiac parameter change corresponds to the type and/or impact of the motion of the subject and the heart activity cardiac parameter change does not correspond to the type and/or impact of the motion of the subject.

18. The system according to claim 15, wherein the computer program product, when executed, causes the processor to perform further operations comprising:

transmitting to the output device a second signal when the TEE cardiac parameter change and the heart activity cardiac parameter change do not correspond to the type and/or impact of the motion of the subject.

19. The system according to claim 15, wherein the computer program product, when executed, causes the processor to perform further operations comprising at least one of:

determining the TEE cardiac parameter change during a third time period, determining the heart activity cardiac parameter change during the third time period, determining that a cardiac parameter change is induced by a change in cardiac status, when the motion of the subject does not exceed a motion threshold during the first time period, and the TEE cardiac parameter change correlates with the heart activity cardiac parameter change, or transmitting to the output device a third signal when the motion of the subject does not exceed the motion threshold during the first time period, and the TEE cardiac parameter change does not correlate with the heart activity cardiac parameter change.

20. The system according to claim 15, wherein the motion sensor is at least one of:

an inertial sensor, a magnetometer, an optical sensor, a radar, an electromyography sensor, a pressure sensor, or a bed pad, an inertial sensor, or a magnetometer included in a device comprising the heart activity sensor, an inertial sensor, or a magnetometer included in the transesophageal echocardiography probe, or a balistocardiograpy, gyrocardiography, or seismocardiography sensor.

* * * * *